United States Patent [19]
Graser

[11] Patent Number: 5,843,085
[45] Date of Patent: Dec. 1, 1998

[54] DEVICE FOR REPAIR OF HALLUX VALGUS

[76] Inventor: Robert E. Graser, 7333 Barlite, Suite 330, San Antonio, Tex. 78224

[21] Appl. No.: 949,876

[22] Filed: Oct. 14, 1997

[51] Int. Cl.⁶ .................................................. A61B 17/56
[52] U.S. Cl. ............................................................. 606/87
[58] Field of Search ................... 606/87, 88, 89, 606/86, 96, 79, 82

[56] References Cited

U.S. PATENT DOCUMENTS

| | | | |
|---|---|---|---|
| 4,565,191 | 1/1986 | Slocum | 128/92 H |
| 4,627,425 | 12/1986 | Reese | 128/92 VY |
| 4,757,810 | 7/1988 | Reese . | |
| 4,952,214 | 8/1990 | Comparetto . | |
| 5,042,983 | 8/1991 | Rayhack . | |
| 5,049,149 | 9/1991 | Schmidt . | |
| 5,053,037 | 10/1991 | Lackey . | |
| 5,112,334 | 5/1992 | Alchermes et al. | 606/87 |
| 5,129,909 | 7/1992 | Sutherland . | |
| 5,147,364 | 9/1992 | Comparetto | 606/85 |
| 5,176,685 | 1/1993 | Rayhack . | |
| 5,344,423 | 9/1994 | Dietz et al. . | |
| 5,364,402 | 11/1994 | Mumme et al. . | |
| 5,413,579 | 5/1995 | Du Toit . | |
| 5,449,360 | 9/1995 | Schreiber . | |
| 5,529,075 | 6/1996 | Clark . | |
| 5,569,260 | 10/1996 | Petersen . | |
| 5,611,802 | 3/1997 | Samuelson et al. . | |
| 5,709,689 | 1/1998 | Ferrante et al. | 606/86 |

*Primary Examiner*—Guy V. Tucker
*Attorney, Agent, or Firm*—Jenkens & Gilchrist, P.C.

[57] ABSTRACT

An osteotomy guide apparatus for assisting in the conduct of Chevron, Youngswick, and Reverdin osteotomy procedures. The osteotomy guide comprises a first and second saw slot converging at an apex. The apparatus further comprises a multiplicity of bone pin holes to firmly fix the osteotomy guide in place and optionally, a visualizer element to indicate to the surgeon the amount of correction which may be expected from the procedure before actual bone cuts are made. The guide may also comprise a first and second stage body which operate in a cooperative fashion to increase the amount of correction and stability provided by any given procedure.

19 Claims, 9 Drawing Sheets

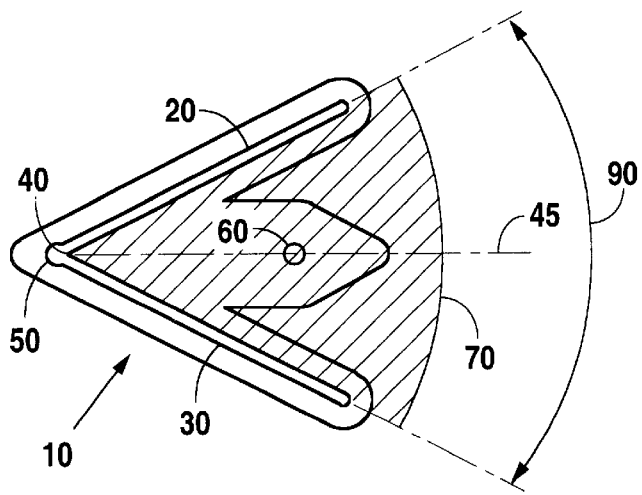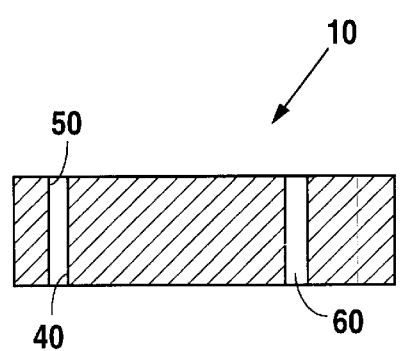
Fig. 1A
Fig. 1B
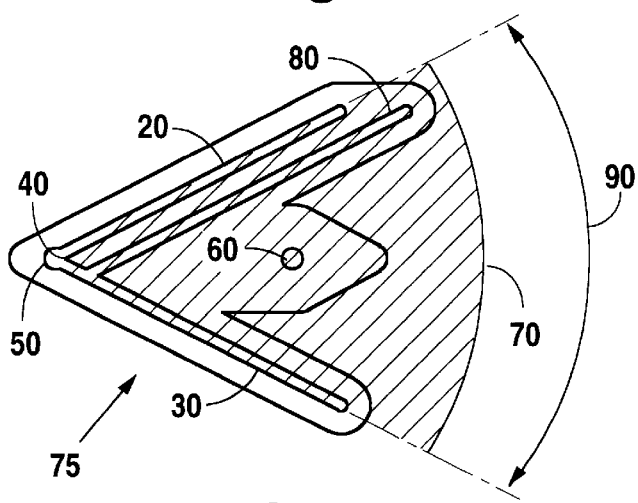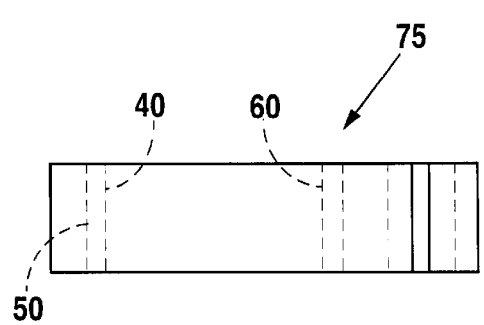
Fig. 2A
Fig. 2B
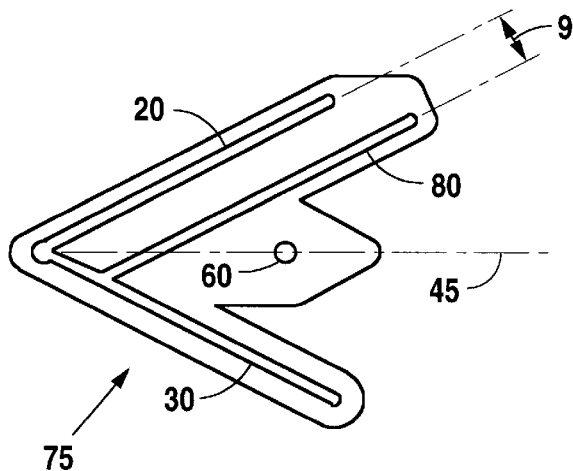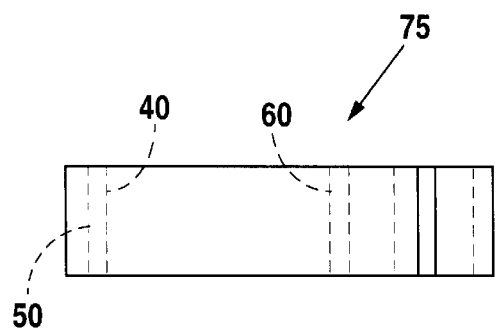
Fig. 2C
Fig. 2D

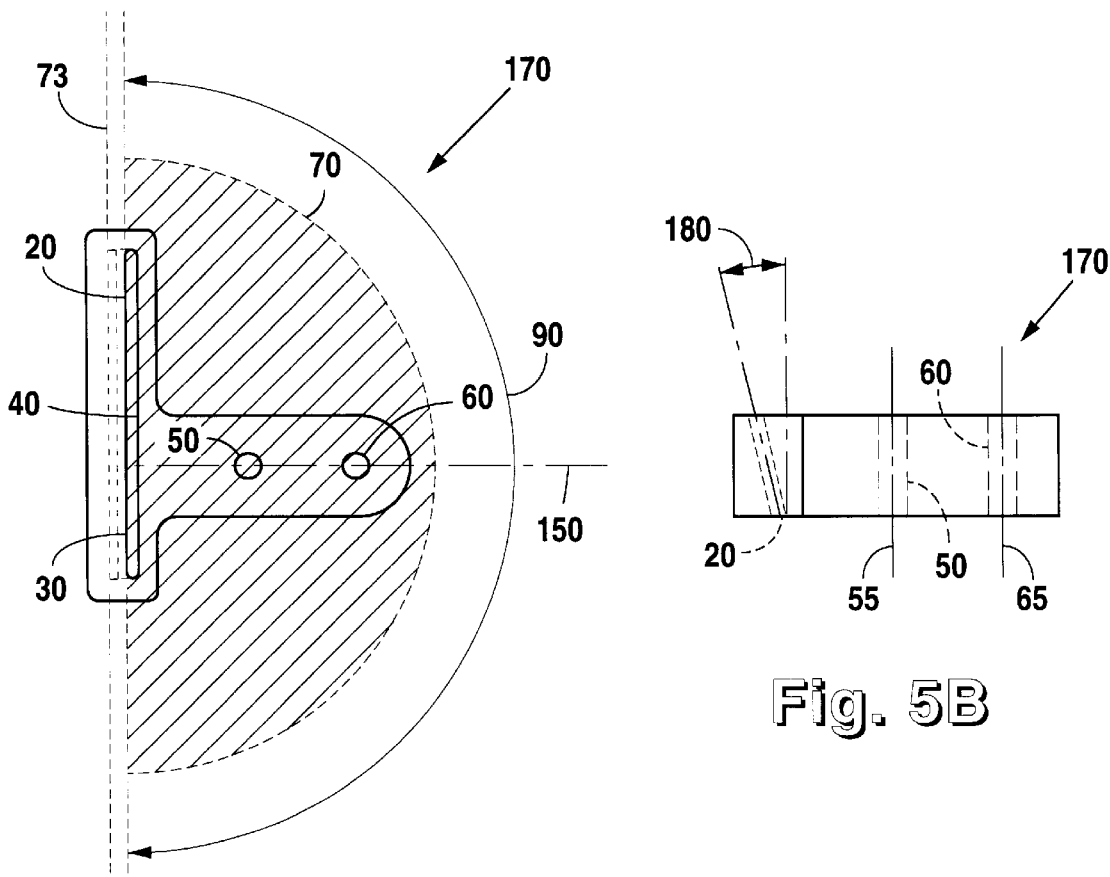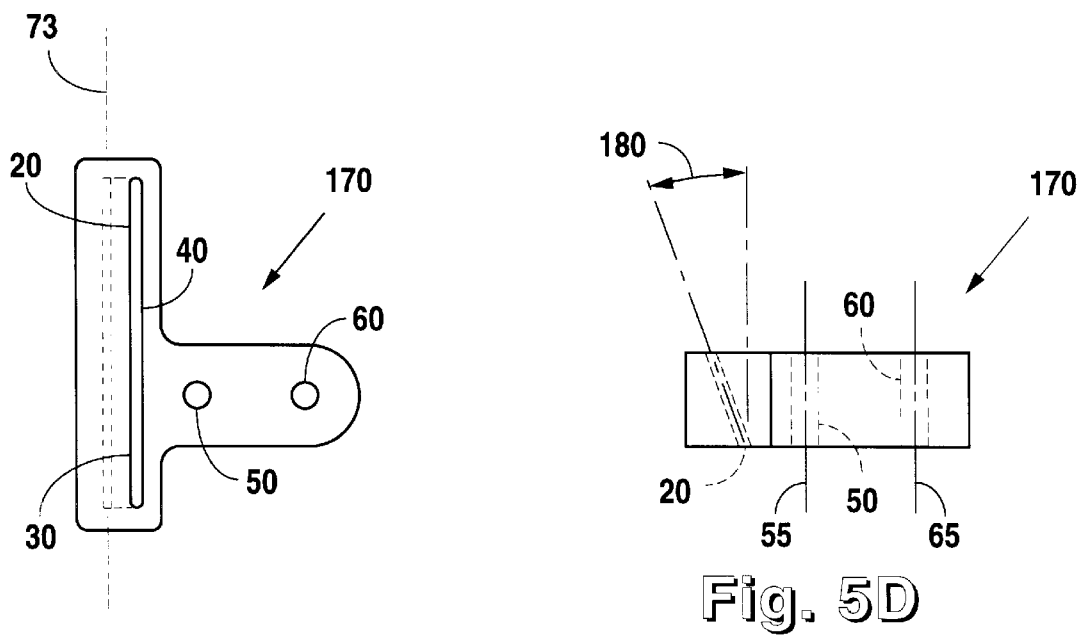

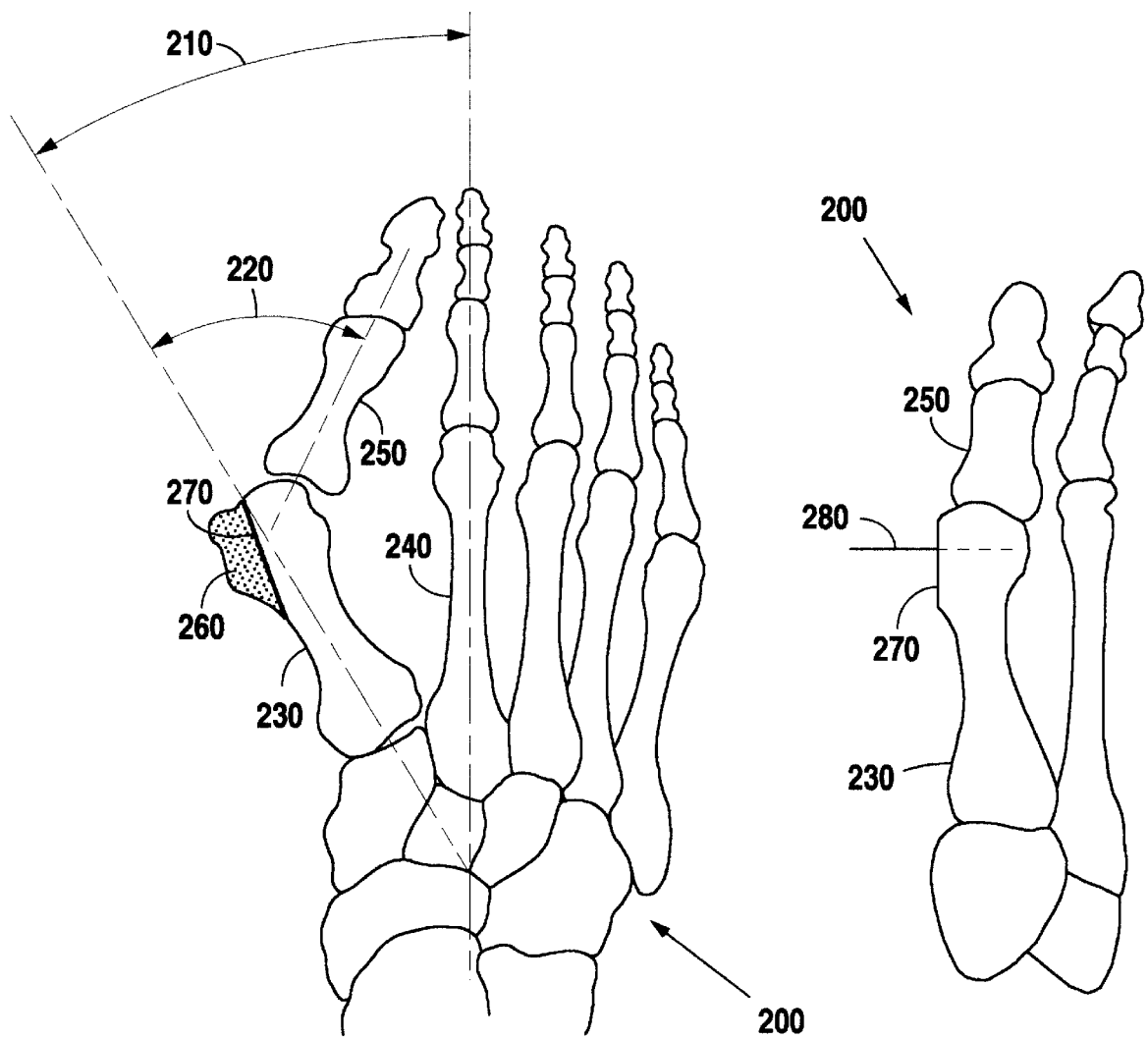
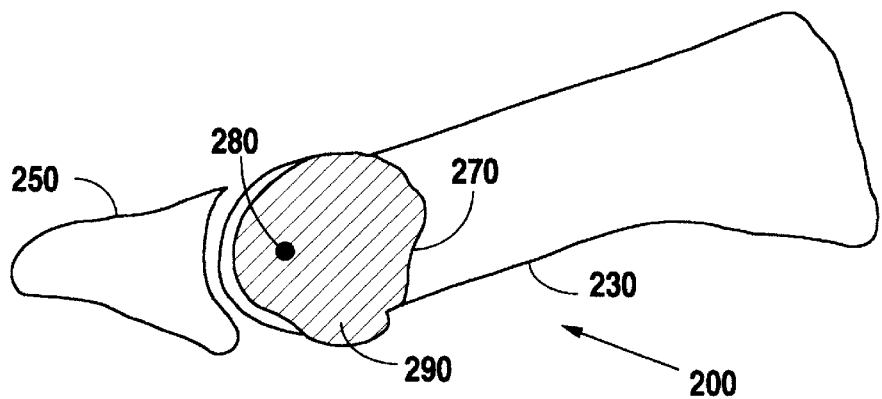
Fig. 6    Fig. 7A
Fig. 7B

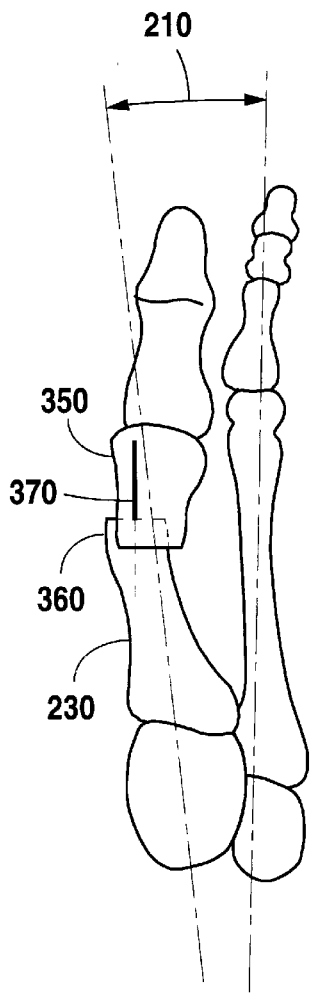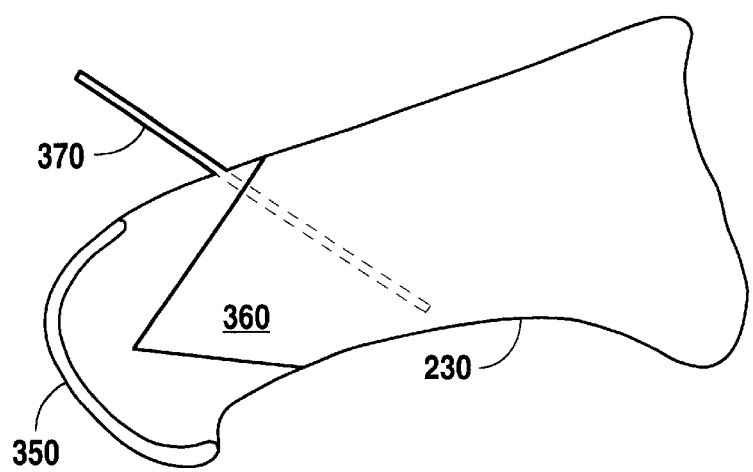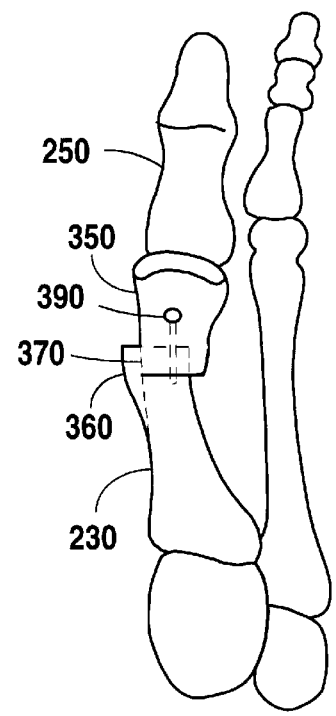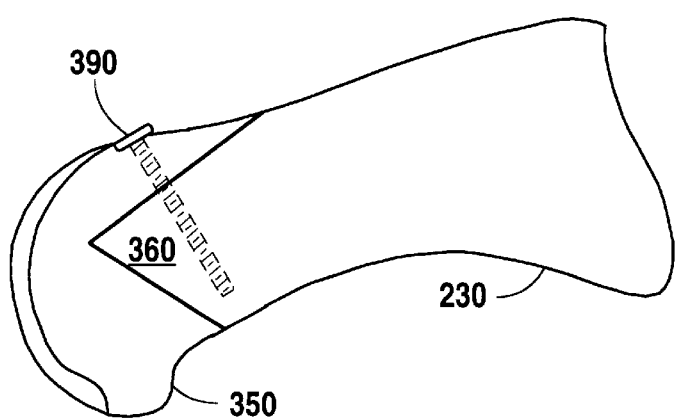
Fig. 10A
Fig. 10B
Fig. 11A
Fig. 11B

DEVICE FOR REPAIR OF HALLUX VALGUS

BACKGROUND OF THE INVENTION

1. FIELD OF THE INVENTION

This invention relates to the field of orthopedic surgery, and more particularly, to devices used to assist in the repair of pronounced bunion deformities, commonly known as hallux valgus.

Hallux valgus has been described as a "static subluxation of the first metatarsophalangeal joint with lateral deviation of the great toe and medial deviation of the first metatarsal." This condition is occasionally accompanied by rotational pronation of the great toe in severe cases.

One of the common causes of hallux valgus is prolonged deformation of the foot brought about by wearing shoes which do not fit properly. In such cases, the great toe is forced into an abnormal orientation for a long period of time, which eventually stretches out the joint capsule, promoting abnormal migration of the muscles. Due to the prevalence of narrow high-heel shoes, women tend to acquire bunions much more commonly than do men. Other factors which may contribute to the condition of hallux valgus include rounded unstable metatarsophalangeal joint surfaces and oblique joint surfaces located at the proximal first metatarsal joint. Once the muscles have migrated laterally outside of the joint line, the hallux valgus deformity reinforces itself and tends to become even more pronounced.

The severity of hallux valgus deformities is usually quantified by taking measurements from x-ray pictures of the foot. One common measurement is the intermetatarsal (IM) angle, which is measured between the line of the first and second metatarsal shafts. The IM angle, in the normal foot, is roughly 6–9 degrees. The second common measurement is the hallux valgus (HV) angle, which is measured between the line of the first metatarsal shaft and the proximal phalanx. The HV angle usually measures about 9–10 degrees. A typical patient having the hallux valgus deformity would have an IM angle of 15°, and an HV angle of 30° (any HV angle greater than 12° would be uniformly regarded as abnormal).

2. DESCRIPTION OF THE RELATED ART

Many procedures exist to correct the hallux valgus deformity. Review of the literature and surgical experience indicate that a five-degree correction of the IM angle and a maximum of ten-degree correction of the HV angle is reproducibly possible using distal osteotomy procedures, of which the most commonly used are the Mitchell, and more recently, the distal Chevron osteotomy. These procedures are most applicable for mild cases of hallux valgus; for more severe cases, the Roger Mann proximal osteotomy of the metatarsal shaft, or the technique patented by Clarke (U.S. Pat. No. 5,529,075), are required. The choice of repair from among the prior art procedures is to some degree guided by the preoperative IM and HV angles. That is, for preoperative angles of 15° or less, and HV angles of 30° or less, a distal Chevron osteotomy is sufficient.

The difficulties involved with hallux valgus repair procedures are many. The main problem which the osteotomy guides of the present invention address is the inability of surgeons to adequately reproduce their osteotomy cuts, case-to-case, and even within the same case. A common occurrence is that the first of the osteotomy cuts in a V-shaped osteotomy, such as the Chevron, is located at a certain pitch and angle with relation to the first metatarsal, and the corresponding second cut (done free-hand) is then very difficult to accomplish at the exact pitch and angle desired by the surgeon for the required correction. Once the bone cuts have been made in this case, the osteotomy, when impacted back on itself, does not precisely fit. The resulting instability makes the bunionectomy site less suitable for weightbearing and increases the chances of nonunion and nonhealing despite internal fixation. Even the act of fixation is very difficult, since attempting to drive a pin or drill and screw through bone that is moving causes problems with fixation alignment, prolonging the surgical case and causing great variations in both long and short-term outcome. Osteotomy cut angles can vary by as many as 20 degrees from case-to-case and surgeon-to-surgeon.

Chevron, Youngswick, and Reverdin osteotomy procedures are all commonly used in the repair of hallux valgus deformities. The decision to use a Youngswick procedure versus a simple Chevron procedure is determined when the patient has a secondary deformity of the hallux valgus known as a hallux limitus/rigidus deformity, which is a limitation of movement at the joint. Many times this is caused by metatarsus primus elevatus, where the first metatarsal is congenitally elevated above the plane of the second metatarsal, thereby producing more pressure at the second metatarsal and a jamming effect as the hallux is prevented from dorsiflexure during the gait cycle. This produces arthritis and pain, as well as increasing the amount of bunion deformity.

The Youngswick procedure is designed to remove a bone wedge from the dorsal aspect of the osteotomy cut, thereby decompressing the joint. As the resulting capital fragment is impacted back on the shaft, it will be plantar flexed from 3 to 5 mm downward, reducing the amount of elevatus plantar flexing so that a normal weight-bearing parabola and increased joint motion are provided. This decompression helps prevent arthritis and is in addition to the secondary plane correction provided by the simple Chevron osteotomy.

The Reverdin procedure improves stability via an L-shaped "stage-one" cut, which provides an almost horizontal plantar shelf produced by the osteotomy, and decreased movement during fixation. The stage-one cut also allows lateral transposition to correct for the intermetatarsal angle in a forefoot bunionectomy. The osteotomy can also be plantar flexed, leaving a small gap between the plantar shelf and the base of the bone, providing correction in up to three planes.

The Reverdin procedure is used in severe bi- and tri-plane deformities of the metatarsal where there is a large hallux abductovalgus angle or hallux abductus angle within the toe caused by a deviated joint at the head of the first metatarsal, also known as the proximal articular set angle. When this angle deviates beyond a range of 0 to 8 degrees (i.e., the normal range), a very high hallux abductus angle results, and must be corrected by removing a pie-shaped wedge from the metatarsal (i.e., the "stage two" cut) to realign the joint in a rectus position that is perpendicular to the long axis of the metatarsal.

The Chevron procedure can also be effected as a two-stage process which allows correction of the proximal articular set and HV angles, as well as adjusting the amount of plantar flexion and transposition. Stage one of the revised Chevron procedure is accomplished in the same manner as is the basic Chevron osteotomy. Stage two of the revised procedure adds removal of a pie-shaped bone wedge from each of the dorsal and plantar Chevron cuts, giving increased mobility in the correction-fixation process, as well as increased stability over the Reverdin osteotomy procedure.

Conducting any of the above-mentioned procedures currently involves the free-hand cutting of bone by the surgeon. Considering the size of the bones involved, and the use of extremely sharp cutting instruments by surgeons with gloved hands, it is easily seen that such cutting procedures are prone to alignment errors and require great care to conduct properly. The present invention is directed toward overcoming this problem. It is desirable to have a device for correcting the hallux valgus deformity which involves a minimal amount of free-hand effort by the surgeon. This reduces the time requited for surgery and also the possibility of error. It is also desirable that any device used to assist in the conduct of such osteotomy procedure be compact, inexpensive to manufacture, user-friendly, and rugged.

SUMMARY OF THE INVENTION

In accord with one aspect of the present invention, an apparatus for assisting in the conduct of a Chevron osteotomy procedure is presented. The Chevron guide body serves to facilitate the angular cuts required for Chevron osteotomies especially in the repair of the hallux valgus deformity. The Chevron osteotomy guide body consists of two saw slots intersecting at an apex, which is coincident with a bone pin hole through which Kirschner wire can be inserted to firmly affix the guide to the bone. The Chevron guide body also provides at least one other bone pin hole to precisely locate the cuts on the bone surface.

Other features of the apparatus include a visualizer element, which allows the surgeon to gauge the amount of correction to be expected from a particular saw cut. The visualizer element is formed so as to fit snugly within the saw slots of the guide body and is used prior to making the actual cut in the bone.

In another aspect of the present invention, an apparatus for assisting in the conduct of the Youngswick osteotomy procedure is presented. In this embodiment of the present invention, the Youngswick guide body comprises the same quantity and arrangement of individual elements as does the Chevron guide body. However, the Youngswick guide body further comprises a third saw slot which runs parallel to the first saw slot and intersects the second saw slot. The parallel distance between the first and third saw slots is variable, to accommodate varied widths of bone wafers which may be extracted from the osteotomy after excision via the third saw slot. The distance is selected according to the surgeon's preference for the amount correction desired. The above-mentioned visualizer element is also accommodated by the Youngswick guide body and can be used to indicate the amount of correction to be effected by the Youngswick osteotomy procedure before actual cuts in the bone are made.

In another aspect of the present invention, an apparatus for assisting in the conduct of the Reverdin osteotomy procedure is presented. The Reverdin stage one guide body also consists of an intersecting pair of saw slots. However, the angle of intersection is quite different from that of the Chevron and Youngswick guide bodies. In addition, none of the bone pin holes are normally located at the apex of the saw slot intersection. In the case of the Reverdin stage one guide body, the bone pin holes are preferably located along a line which is perpendicular to the first saw slot and within the arcuate area swept out by both saw slots. The visualizer element is also accommodated by the saw slots of the Reverdin guide for use by the surgeon in visualizing the amount of correction to be effected by Stage one of the Reverdin procedure.

In another aspect of the present invention, a supplementary apparatus to assist in the conduct of the Reverdin osteotomy procedure is presented. A Reverdin stage one body, comprising a pair of saw slots which intersects so as to form a continuous single slot, can be used in the second stage of the Reverdin osteotomy procedure to extract a pie-shaped wedge of bone for correction of severe hallux valgus deformities. The Reverdin stage two body is designed to accommodate the same bone pin hole locations as used by the Reverdin stage one guide body. In use, the Reverdin guide body is fixed in place with two or more Kirschner wires and the Stage one osteotomy is made. After the first osteotomy is complete, the Reverdin stage one guide body is removed and the Reverdin stage two body is put into place, to effect a second osteotomy and complete Stage two of the Reverdin procedure. As is the case with all of the osteotomy apparatus described, the visualizer element can also be accommodated by the saw slots in the Reverdin stage two body.

Another aspect of the present invention provides two different guide bodies for effecting a two stage (revised) Chevron osteotomy procedure. The Chevron stage one guide body is similar to the previously described basic Chevron guide body, but has an elongated central component to which is added an additional bone pin hole. While stage one of the revised Chevron procedure is carried out as per the basic Chevron procedure, an additional Kirschner wire is inserted into the third bone pin hole and is left in place after the Chevron stage one guide body and first Kirschner wire are removed. The Chevron stage two guide body is also similar in appearance to the basic Chevron guide, but instead of vertical saw slots (parallel to the center lines of the bone pin holes), the Chevron stage two guide has saw slots which are angled away from the center lines of the bone pin holes. In addition, the bone pine holes of the Chevron stage two guide are located so as to coincide with the second and third bone pin holes of the Chevron stage one guide, so that the Chevron stage two guide can be placed over the second and third Kirschner wires left in place after stage one of the revised Chevron procedure has been accomplished. It should be apparent to those skilled in the art that the adjustment process involved in stages one and two of the revised Chevron procedure is analogous to that involved in stages one and two of the Reverdin procedure.

Other features of the apparatus include the ability to use the visualizer element as a preventative measure; the visualizer can be placed within the saw slot of the Reverdin stage two body during Stage two of the Reverdin procedure to prevent incursion of the saw into the medial shelf created during the Stage one Reverdin osteotomy procedure.

BRIEF DESCRIPTION OF THE DRAWINGS

FIGS. 1A and 1B are top and side views, respectively, of the (Chevron) osteotomy guide of the present invention.

FIGS. 2A and 2B are top and side views, respectively, of an alternative embodiment of the osteotomy guide of the present invention.

FIGS. 2C and 2D are top and side views, respectively, of an alternative embodiment of the osteotomy guide of the present invention.

FIGS. 5A and 5B are bottom and side views, respectively, of an alternative embodiment of the osteotomy guide of the present invention.

FIGS. 5C and 5D are bottom and side views, respectively, of an alternative embodiment of the osteotomy guide of the present invention.

FIG. 6 is a dorsal view of the bones of an abnormal right forefoot with the intermetatarsal and hallux valgus angles indicated.

FIGS. 7A and 7B are dorsal and medial views, respectively, of the forefoot after the medial eminence of the first metatarsal shaft has been excised, and the first K-wire inserted.

FIGS. 10A and 10B are dorsal and medial views, respectively, of the first metatarsal shaft after the correctly aligned capital fragment has been fixed in place.

FIGS. 11A and 11B are dorsal and medial views, respectively, of the correctly aligned first metatarsal shaft after insertion of a fixating screw.

DESCRIPTION OF THE PREFERRED EMBODIMENT

Figure 3A:
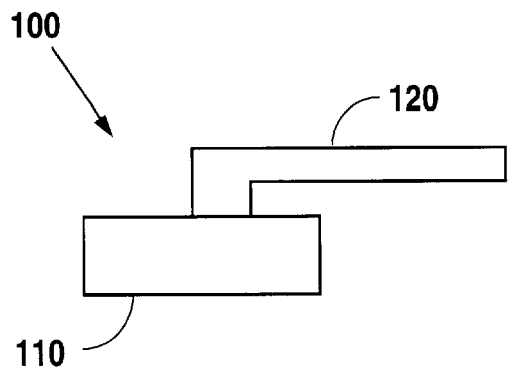
FIGS. 3A and 3B are side and front views, respectively, of the visualizer element for the osteotomy guide of the present invention.

FIG. 1 illustrates one embodiment of the osteotomy guide of the present invention. In this particular instance, the embodiment is useful for making Chevron osteotomies. The Chevron guide body 10 is preferably fabricated from stainless steel, but can be made from any other material which is relatively hard, impervious to damage by accidental contact with an osteotomy saw blade, non-corrosive, and biocompatible. First saw slot 20 and second saw slot 30 converge at apex 40, which is also coincident with first bone pin hole 50.

First saw slot 20 and second saw slot 30 sweep out an osteotomy angle 90 of about 180° or less. More preferably, the swept out angle 90 should be from about 40° to about 60° for execution of a Chevron osteotomy, and most preferably, the osteotomy angle 90 should be approximately 55°. Second bone pin hole 60 should be located somewhere within the planar arcuate area 70 swept out by the intersection of first saw slot 20 and second saw slot 30. Most preferably, second bone pin hole 60 is located along bisecting line 45, an imaginary line that bisects the planar arcuate area 70 described previously. While there may be a multiplicity of bone pin holes, exemplified by first bone pin hole 50 and second bone pin hole 60, the invention requires at least two such holes to properly affix Chevron guide body 10 to the osteotomy site. Other bone pin holes, through which Kirschner wires (i.e., K-wires) may be inserted, will normally be located within and perpendicular to, planar arcuate area 70.

FIG. 1B illustrates a side view of the Chevron guide body 10. Here it can be seen that first bone pin hole 50 is located slightly behind apex 40 such that the circumference of first bone pin hole 50 is coincident with apex 40. Additionally, it should be noted that first saw slot 20 and second saw slot 30 are cut vertically through Chevron guide body 10. That is, a saw blade entering directly through first saw slot 20 will never intersect with a similar saw blade entering second saw slot 30. In the case of a mild hallux valgus condition, such parallel, non-converging saw blade entry is all that is necessary for producing a corrective Chevron osteotomy.

FIGS. 2A and 2B illustrate top and side views of an alternative embodiment of the osteotomy guide of the present invention, respectively. In FIG. 2A, a guide which is useful for effecting a Youngswick osteotomy is illustrated. Youngswick guide body 75 also contains first saw slot 20 and second saw slot 30, which intersect at apex 40. First bone pin hole 50 is also coincident with apex 40, as described previously in the case of Chevron guide body 10. The location of second bone pin hole 60 is determined as described previously, and normally resides within and perpendicular to the planar arcuate area 70 formed by the intersection of first saw slot 20 and second saw slot 30. Again, osteotomy angle 90 can be set to any angle of 180° or less, but is more preferably fixed at from about 40° to about 60°, and is most preferably fixed at approximately 55°. In this embodiment of the invention, Youngswick guide body 75 further comprises third saw slot 80, which originates at some point along second saw slot 30 and continues on for some distance in parallel with first saw slot 20. FIG. 2C illustrates another embodiment of the osteotomy guide (i.e., Youngswick guide body 75); it can be seen in this illustration that Youngswick distance 95, which is the parallel distance between first saw slot 20 and third saw slot 80, can be varied to accommodate the need for greater or lesser adjustment in the Youngswick osteotomy procedure. FIGS. 2B and 2D illustrate side views of the Youngswick guide body 75 embodiments of the present invention, respectively.

Figure 3B:
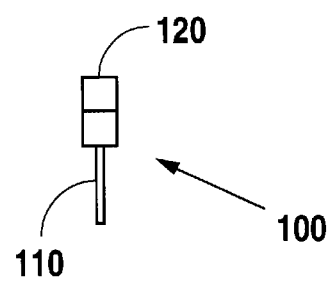

In FIGS. 3A and 3B, visualizer 100, which is an optional element of the osteotomy guide of the present invention, can be seen. Visualizer 100 further comprises key 110 and indicator arm 120. Key 110 is preferably fashioned so as to fit snugly within first saw slot 20 or second saw slot 30 of Chevron guide body 10, and alternatively, within first saw slot 20, second saw slot 30, or third saw slot 80 of Youngswick guide body 75. In use, visualizer 100 is positioned so that key 110 is fitted into one of the aforementioned saw slots (20, 30, or 80) and indicator arm 120 extends outwardly away from apex 40 along the axis of the selected saw slot.

Indicator arm 120 extends beyond the end of the selected guide body (10 or 75) for some distance, and is used to create a visual reference for the surgeon so that the extent of the osteotomy correction can be seen before any bone cuts are made. Indicator arm 120 is formed so that it prevents visualizer 100 from slipping completely through the saw slot into which it is placed. The bottom of visualizer 100, key 110, rests against the patient's bone structure and serves as an additional obstacle to migration of visualizer 100 through the selected saw slot.

Figure 4A:
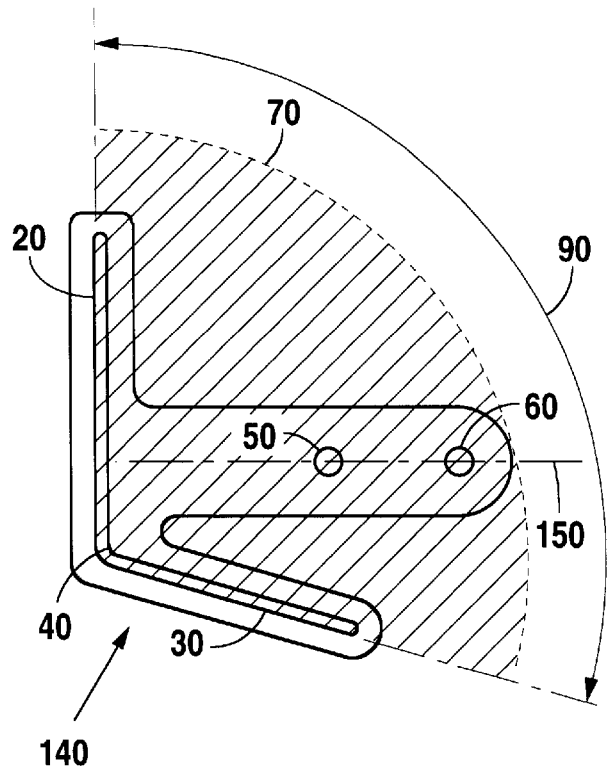
FIGS. 4A and 4B are bottom and side views, respectively, of an alternative embodiment of the osteotomy guide of the present invention.
Figure 4B:
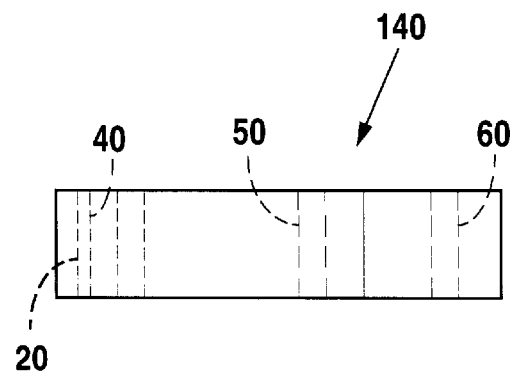

Turning now to FIGS. 4A and 4B, the bottom and side views, respectively, of an alternative embodiment of the osteotomy guide of the present invention can be seen. This particular embodiment facilitates the Reverdin osteotomy procedure. Reverdin stage one guide body 140 is also characterized by the intersection of first saw slot 20 and second saw slot 30 at apex 40, as are the Chevron guide body 10 and Youngswick guide body 75. Similarly, first bone pin hole 50 and second bone pin hole 60 are required to properly fix the Reverdin guide body in place during use. However, due to the nature of the procedure, bone pin holes 50 and 60 are now located along a perpendicular line 150 which originates at some point along first saw slot 20 and penetrates into the planar arcuate area 70 swept out by first saw slot 20 and second saw slot 30. While not absolutely necessary for the use of the invention, it is preferred that first bone pin hole 50 and second bone pin hole 60 are both located along perpendicular line 150. However, it is possible to effectively construct the Reverdin stage one guide body 140 so that bone pin holes 50 and 60 are not located along perpendicular line 150, but are somewhere else within the planar arcuate area 70. While osteotomy angle 90 may again be 180° or less, it is preferred that osteotomy angle 90 measures from about 95° to about 115°, and it is most preferred that osteotomy angle 90 is fixed at approximately 105°.

FIGS. 4A and 4B illustrate an embodiment of the osteotomy guide which is used during the first stage of the Reverdin surgical osteotomy procedure. The osteotomy guide embodiment used in the second stage of the Reverdin procedure is illustrated in FIGS. 5A and 5B, which show bottom and side views of Reverdin stage two body 170, respectively. In this case, osteotomy angle 90 is equal to 180° and, therefore, first saw slot 20 and second saw slot 30 form a continuous single saw slot opening. There is no bone pin hole located at apex 40, but as is the case with Reverdin stage one guide body 140, first bone pin hole 50 and second bone pin hole 60 are located within the 180° planar arcuate area 70 swept out by the intersection of first saw slot 20 and second saw slot 30. Perpendicular line 150 extends into and is coplanar with the arcuate area 70, originating at some point along first saw slot 20 or second saw slot 30, depending on whether the Reverdin stage two body 170 is to be used on the left or right foot, respectively. Of course, it is also possible to locate perpendicular line 150 at the apex of first and second saw slots 20 and 30. As is more clearly apparent in FIG. 5B, first and second saw slots 20 and 30 are cut at an angle, Reverdin angle 180, into Reverdin stage two body 170. This is in contrast to the other illustrated embodiments, in which first saw slot 20, second saw slot 30, and third saw slot 80 are all vertical, running in a direction parallel to first center line 55 of first bone pin hole 50 and the second center line 65 of the second bone pin hole 60 and perpendicular to arcuate area 70.

Reverdin stage two body 170 is formed so that it may be used on the same patient (during Stage two of the Reverdin procedure), directly after Reverdin stage one guide body 140 (used during Stage one of the Reverdin procedure), if the surgeon so desires. A pair of bone pin holes, first bone pin hole 50 and second bone pin hole 60 are located on Reverdin stage two body 170 so that they coincide directly (i.e. are coincident) with the first and second center lines 55 and 65 of a selected pair of bone pin holes, first bone pin hole 50 and second bone pin hole 60 of Reverdin stage one guide body 140. In use, Reverdin stage two body 170 can be placed directly over the same K-wires used to fix the Reverdin stage one guide body 140 in place. When overlaid in this manner, the exit path 73 of the Reverdin stage two body 170 is located so as to parallel the location of the entry path 72 of the Reverdin stage one guide body 140. However, the exit path 73 is offset by some distance (preferably about 2–5 mm, depending on the amount of correction needed) from the entry path 72. As will be demonstrated subsequently, Reverdin stage two body 170 is used to effect the second stage of the Reverdin osteotomy procedure, which removes a pie-shaped wedge from the metatarsal using artifacts left behind by the surgeon after use of the Reverdin stage one guide body 140. FIGS. 5C and 5D illustrate an alternative embodiment of Reverdin stage two body 170 in which Reverdin angle 180 has been increased to accommodate greater corrections in the hallux valgus condition, as desired by the physician. All other elements of this particular embodiment are identical to that illustrated in FIGS. 5A and 5B.

FIG. 6 illustrates a dorsal view of the bones of an abnormal foot 200 afflicted by the hallux valgus condition. IM angle 210 and HV angle 220 are indicated. That is, it can be clearly seen that the IM angle 210 is the angle swept out by the first metatarsal 230 and second metatarsal 240. The HV angle is described by the intersection of the median axis of the first metatarsal, as it intersects with the median axis of the first phalangeal bone 250.

In accordance with the practice of the instant invention as used in a Chevron osteotomy procedure, the medial eminence 260 of the first metatarsal 230 is exposed and excised along eminence resection line 270. Exposure of the medial eminence 260 is effected by performing a soft tissue release through a medial incision or dorsal medial incision at the first metatarsal, per the surgeon's preference. This is followed by a capsulotomy of the tibial side of the metatarsophalangeal joint. The medial eminence 260 of the first metatarsal 230 head is then deeply exposed and excised.

Turning now to FIGS. 7A and 7B, it can be seen that flat surface 290 is created by excising the medial eminence 260. Flat surface 290 is located along the medial aspect of the distal first metatarsal 230 bone. Once medial eminence 260 has been excised, the surgeon places a 0.045 dia. first K-wire 280 into the first metatarsal at some location on the flat surface 290 where it is desired to locate the apex of the intended Chevron osteotomy. Other sizes of K-wire may also be used, per the surgeon's preference.

Figure 8A:
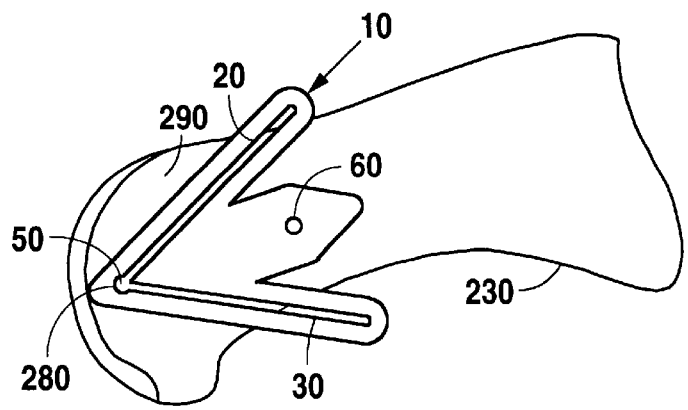
FIG. 8A is a medial view of the first metatarsal shaft with the osteotomy guide of the present invention applied over the first K-wire.
Figure 8B:
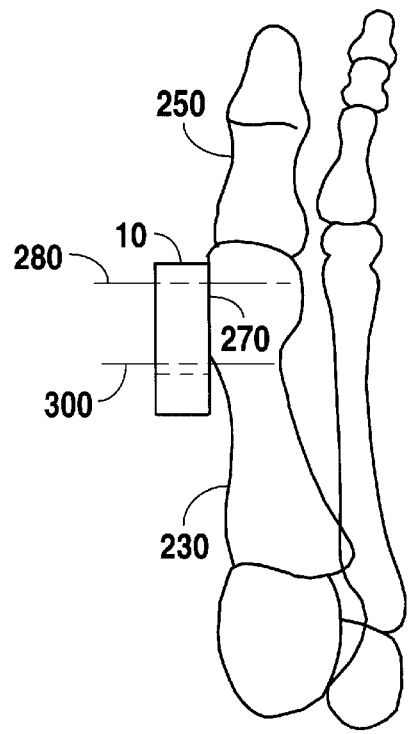
FIG. 8B is a top view of the osteotomy guide of the present invention pinned in place on the first metatarsal shaft.

Turning now to FIG. 8A, placement of the Chevron guide body 10 can be seen. First bone pin hole 50 is penetrated by first K-wire 280 and Chevron guide body 10 is located so as to directly contact flat surface 290. The exact location of first saw slot 20 and second saw slot 30 can then be visualized, and once the surgeon locates the future cuts precisely, second K-wire 300 is inserted into first metatarsal 230 through second bone pin hole 60 to firmly fix Chevron guide body 10 in place against flat surface 290. If further stability of the Chevron guide body 10 is desired, a mosquito hemostat may be attached to first K-wire 280 and/or second K-wire 300 to firmly fix Chevron guide body 10 against flat surface 290 (not shown). FIG. 8B depicts Chevron guide body fixed in place by first K-wire 280 and second K-wire 300.

A sagittal saw, or equivalent, is placed within first saw slot 20 and second saw slot 30 to cut down and through first and second slots 20 and 30 into first metatarsal 230 to form the Chevron osteotomy. First and second saw slots 20 and 30 are most preferably 0.5 mm wide, so as to accommodate a 0.5 mm sagittal saw blade. The osteotomy is most effectively performed by cutting along the entire distance of first and second saw slots 20 and 30, until the first K-wire 280, located at apex 40 is encountered.

Figure 9A:
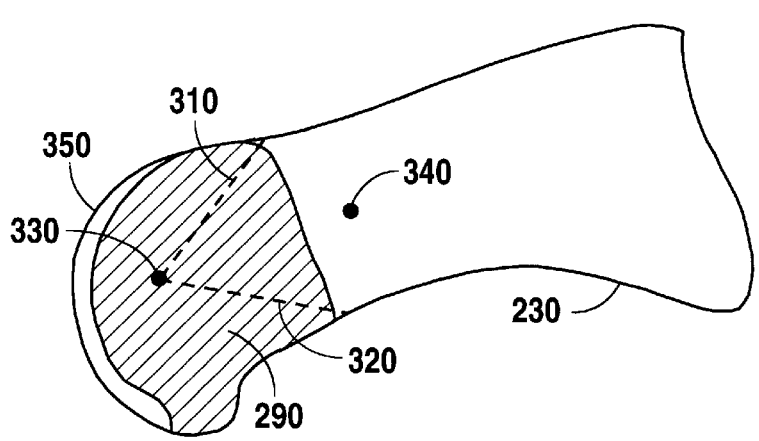
FIG. 9A is a medial view of the first metatarsal shaft after the osteotomy has been completed and the K-wires have been removed.
Figure 9B:
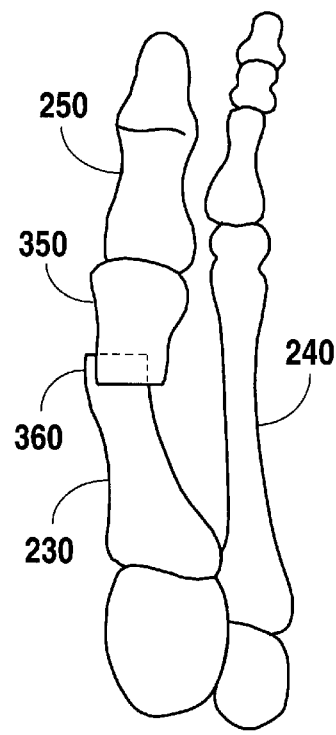
FIG. 9B is a dorsal view of the first metatarsal osteotomy after manipulation to effect corrective alignment.

Turning now to FIG. 9A, the first metatarsal 230 is depicted after the osteotomy is complete and Chevron guide body 10 has been removed. First and second K-wires 280 and 300 have also been removed to form first K-wire hole 330 and second K-wire hole 340, respectively. First saw cut 310 and second saw cut 320, created by insertion of a sagittal saw into first saw slot 20 and second saw slot 30, respectively, are also shown.

Once the osteotomy is complete, the surgeon utilizes manual pressure on capital fragment 350 for lateral transposition toward the second metatarsal 240 to a point of correction deemed appropriate by the surgeon. At this time, capital fragment 350 is impacted upon the first metatarsal 230 shaft.

A temporary fixating K-wire 370 is inserted into capital fragment 350 and first metatarsal 230 so as to solidly fixate the osteotomy in place. Fixating K-wire 370 is inserted from a dorsal distal position to a plantar proximal position in preparation for screw fixation. FIG. 10B clearly illustrates the fixating K-wire 370 in place, as the capital fragment 350 has been properly located along the surface of medial shelf 360.

Turning now to FIG. 11A, the placement of a 2.0 mm or 2.7 mm screw, preferably, is shown. Fixating screw 390 is used to effect permanent fixation of the osteotomy so that temporary fixating K-wire 370 can be removed. Insertion of fixating screw 390 is effected using standard surgical techniques. FIG. 11A illustrates the relative locations of fixating K-wire 370 and fixating screw 390. FIG. 11B illustrates a lateral view of first metatarsal 230 after permanent fixation by fixating screw 390 and removal of fixating K-wire 370.

Figure 12A:
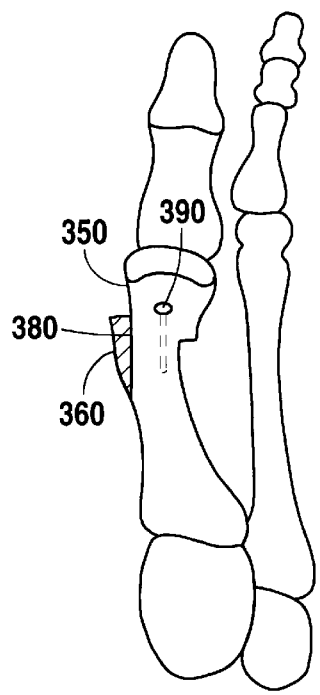
FIG. 12A is a dorsal view of the first metatarsal shaft indicating the portion of the medial shelf (created by the osteotomy) which is to be excised.
Figure 12B:
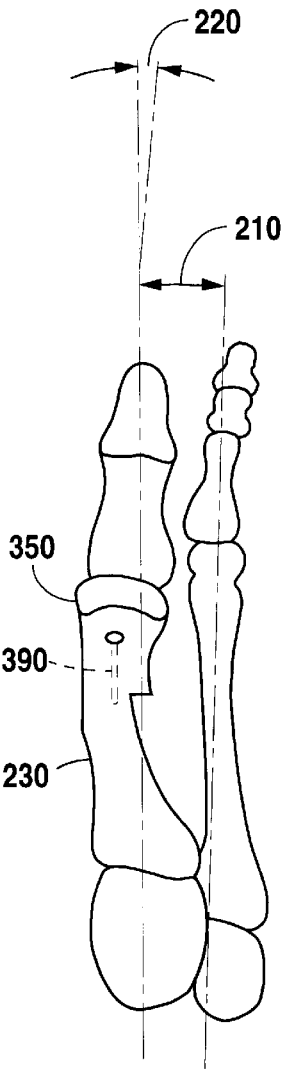
FIG. 12B is a dorsal view of the completed corrective repair of the first metatarsal shaft.

Turning now to FIG. 12A, the shelf resection line 380 can be clearly seen. The medial shelf 360 of bone created by transposition of the capital fragment 350 is now cut away along shelf resection line 380, preferably utilizing a sagittal saw, creating a smooth surface along the proximal side of the first metatarsal 230. FIG. 12B illustrates a dorsal view of the foot 200 after the Chevron osteotomy procedure has been completed. It can be easily seen that the IM angle has now been normalized and the HV angle is drastically reduced.

Figure 13:
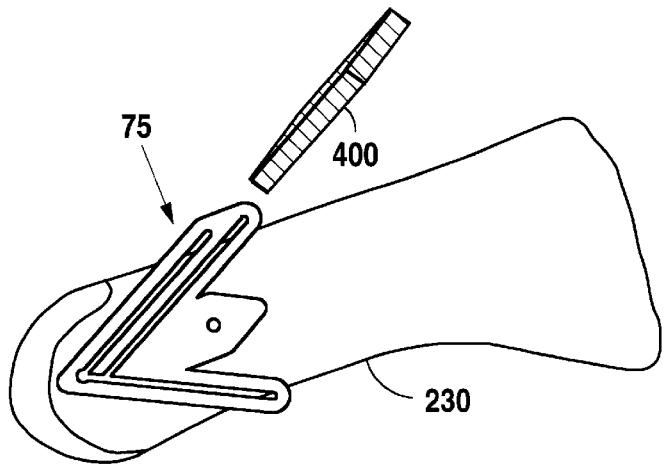
FIG. 13 is a perspective view of the first metatarsal shaft with an alternative embodiment of the osteotomy (Youngswick) guide of the present invention applied over the first K-wire.

FIG. 13 illustrates use of the Youngswick guide body 75 when the surgeon has decided that a Youngswick osteotomy is the most appropriate corrective procedure. As in the Chevron osteotomy procedure, the Youngswick guide body 75 is secured to first metatarsal 230 by the use of first and second K-wires 280 and 290 inserted into first and second bone pin holes 50 and 60. However, an additional cut into the bone of first metatarsal 230 is made via third saw slot 80. This has the effect of creating a Chevron osteotomy with an additional wafer of bone to be excised. Bone wafer 400 is created by the intersection of first saw slot 20 and third saw slot 80 with second saw slot 30. Once the Youngswick guide body 75 is removed and the osteotomy is complete, the capital fragment 350 created by the osteotomy is then impacted upon the first metatarsal 230 to provide a transposed relocation of the capital fragment 350, and additionally, a lowered location of the capital fragment 350 in relation to the first metatarsal 230. The choice of guides to use is made by the surgeon preoperatively based on x-rays as previously mentioned. However, it is often not until the wound is opened and the joint can be directly visualized (since the cartilage orientation cannot be adequately viewed on an x-ray) that the proper procedure will be known. The Chevron guide and Youngswick guide systems are designed to be used concurrently, so that if a surgeon has committed a Chevron cut, but later determines that more joint motion is needed, he can position a Youngswick guide of varying correctability over the same K-wires used to fix the Chevron guide in place, and perform a second osteotomy cut to reduce the hallux limitus/rigidus component.

Figure 14:
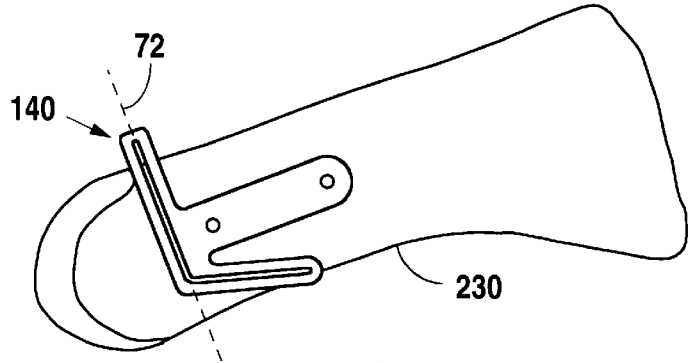
FIG. 14 is a perspective view of the first metatarsal shaft with an alternative embodiment of the osteotomy (Reverdin-Stage one) guide of the present invention applied over the first K-wire.
Figure 15:
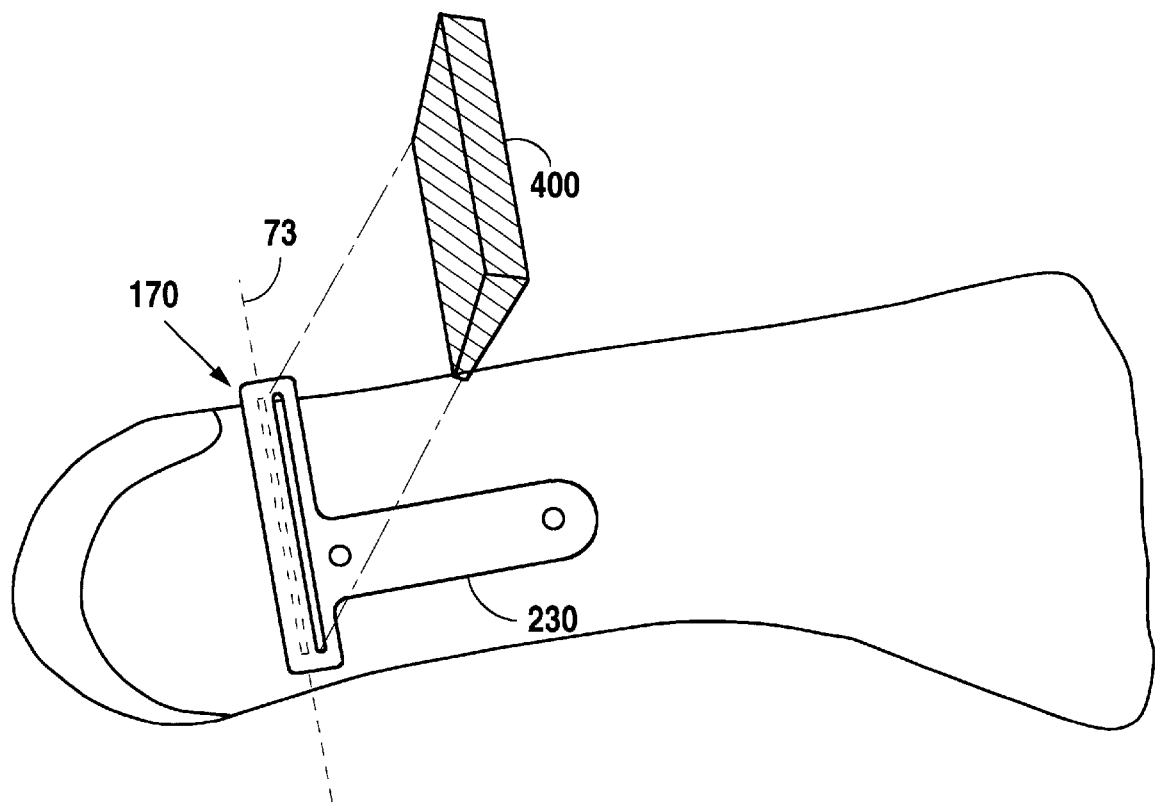
FIG. 15 is a perspective view of the first metatarsal shaft with an alternative embodiment of the osteotomy (Reverdin-Stage one) guide of the present invention applied over the first K-wire.

FIGS. 14 and 15 illustrate the use and placement of the Reverdin stage one guide body 140 and Reverdin stage one body 170, respectively. In FIG. 14, it can be seen that placement of the Reverdin stage one guide body 140 on the first metatarsal 230 after resection of the medial eminence 260 is quite similar to placement of the Chevron guide body 10 and Youngswick guide body 75. As mentioned previously, the Reverdin procedure is chosen by the surgeon when tri-plane correction is needed. As is the case with the Chevron guide body 10 and the Youngswick guide body 75, once Reverdin stage one guide body 140 is fixed in place using first and second K-wires 280 and 300 inserted into first and second bone pin holes 50 and 60, the osteotomy can be easily effected by the surgeon by inserting a sagittal or oscillating saw, or equivalent, into the first and second saw slots 20 and 30. Use of mosquito hemostats to secure the Reverdin stage one guide body 140 against the flat surface 290 is optional.

Because the requirements of the Reverdin procedure are somewhat different than those of the Chevron and Youngswick procedures, use of the Reverdin stage two body 170 may be optionally indicated as determined by the surgeon. FIG. 15 illustrates placement of the Reverdin stage two body 170 against flat surface 290 after the Reverdin stage one guide body 140 has been removed and the first osteotomy has been completed. As can be clearly seen in FIG. 15, Reverdin stage two body 170 is designed so as to fit directly over first and second K-wires 280 left in place after removal of the Reverdin stage one guide body 140. Reverdin angle 180 employed by Reverdin stage two body 170 is selected so as to provide, preferably, a base width of two, three, or four millimeters of bone to removed along the length of first saw cut 310. Bone wafer 400 in this case is no longer rectangular in shape (as for the Youngswick procedure), but is pie-shaped. This is caused by the angular cut effected by use of the Reverdin stage two body 170. In the case of the Youngswick guide body 75, first saw slot 20 and third saw slot 80 are parallel, so the bone wafer 400 removed will have parallel sides. Since the entry path 72 of the first saw slot 20 of Reverdin stage one guide body 140 and the exit path 73 of the saw slots in the Reverdin stage two body 170 are non-parallel, and offset, the bone wafer 400 subsequently removed will have non-parallel sides. The shape of the wafer removed is dictated by the requirements of the Reverdin osteotomy procedure and the amount of correction necessary.

Figure 16:
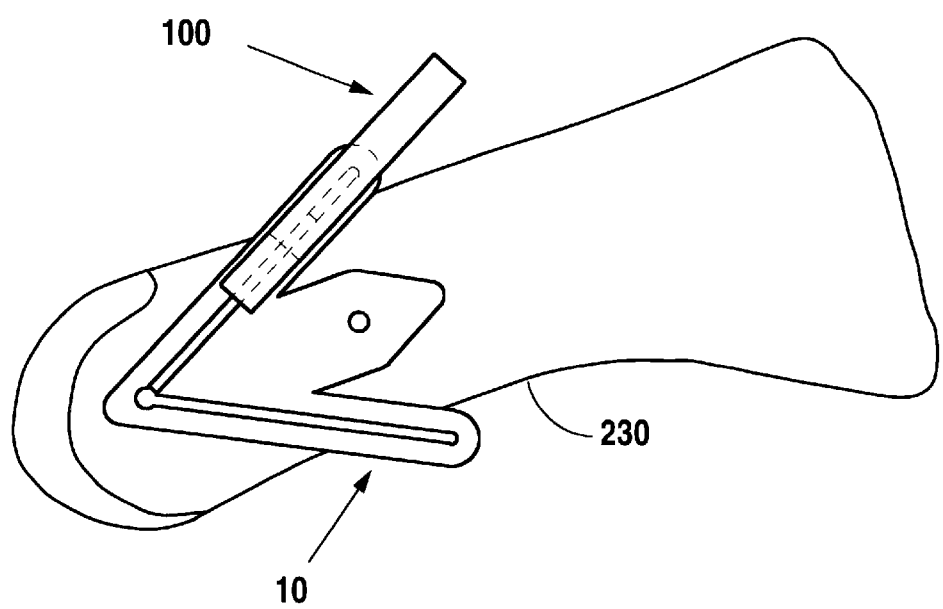
FIG. 16 is a medial view of the visualizer element of the present invention as applied to the Chevron osteotomy guide body.

FIG. 16 illustrates use of visualizer 100 with the Chevron guide body 10. Visualizer 100 can be inserted into any of the saw slots (20, 30, or 80) of the osteotomy guides of the present invention. Visualizer 100 is intended to temporarily reside in any one of the selected saw slots so that the surgeon can determine the amount of correction which will occur when a particular cut is made. That is, visualizer 100 extends along the line of the cut and for some distance beyond the guide body, making it easy for the surgeon to visualize the amount of correction which will occur. Specifically, visualizer 100 can be used with either the Chevron guide body 10, Youngswick guide body 75, Reverdin stage one guide body 140, or the Reverdin stage two body 170. By way of experimentation, it has been determined that visualizer 100 is also useful during the second stage of the Reverdin osteotomy procedure as a preventative measure. During the second stage of the process, in which the bone wafer 400 is excised using the Reverdin stage two body 170, key 110 of visualizer 100 can be inserted into the end of second saw slot 30 of Reverdin stage two body 170 to prevent incursion into the plantar shelf created by the first stage osteotomy previously effected (by use of the Reverdin stage one guide body 140).

Figure 17A:
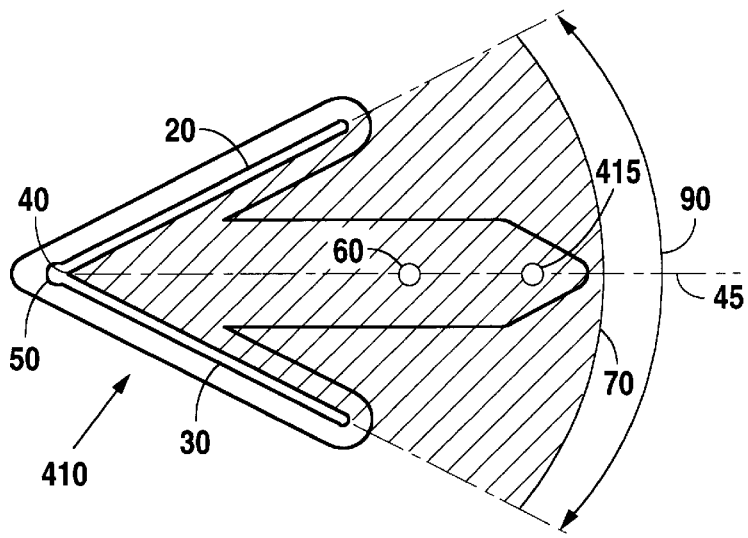
FIGS. 17A–17C are top views of the (Chevron stages one and two) osteotomy guides of the present invention.

As mentioned previously, the Chevron osteotomy procedure can be performed in two stages to give increased corrective ability, as well as stability. The Chevron stage 1 guide body 410 (shown in FIG. 17A) is very similar to the Chevron guide body 10 illustrated in FIG. 1. First saw slot 20 and second saw slot 30 converge at apex 40, which is also coincident with the first bone pin hole 50. The osteotomy angle 90 swept out by the first and second saw slots 20 and 30 will be about 180° or less. More preferably, the swept out angle 90 should be from about 40° to about 60° for execution of a Chevron osteotomy, and most preferably, the osteotomy angle 90 should be approximately 55°. Second bone pin hole 60 should be located somewhere within the planar arcuate area 70 swept out by the intersection of first saw slot 20 and second saw slot 30. Most preferably, second bone pin hole 60 is located along bisecting line 45, an imaginary line that bisects the planar arcuate area 70 described previously. In the Chevron stage 1 guide body 410, there is also a third bone pin hole 415 located along the bisecting line 45. Other bone pin holes, through which additional Kirschner wires (i.e., K-wires) may be inserted, are located within planar arcuate area 70.

In use, the Chevron stage 1 guide body 415 is applied in the same way as shown for the Chevron guide body 10 in FIGS. 8A and 8B. However, in the case of the two-stage Chevron procedure, a third K-wire is inserted through third bone pin hole 415 before the Chevron stage one guide body 415 and the first K-wire 280 are removed from the site of the osteotomy (after the first Chevron cut is made). This pair of bone pin holes, first and second bone pin holes 430 and 440 of the Chevron stage two guide body 420 (shown in FIGS. 17B and 17C), are designed to coincide (i.e. be coincident) with the second and third bone pin holes 60 and 415 of the Chevron stage one guide, so that they can then placed over the K-wires originally inserted through the second and third bone pin holes 60 and 415 of the Chevron stage one guide body 410, respectively.

Figure 17B:
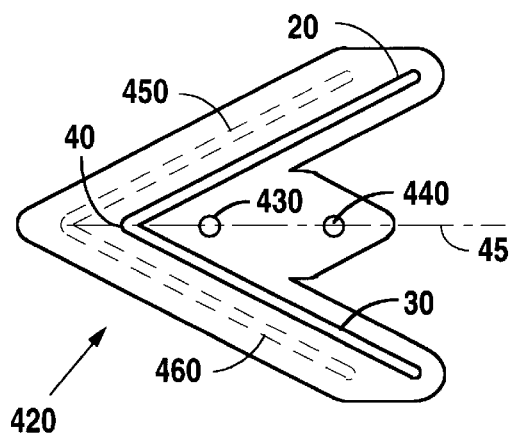

FIG. 17B illustrates a top view of the Chevron stage two guide body 420. While a pair of saw slots, first saw slot 20 and a second saw slot 30, converge at an apex 40, it can be seen that the apex 40 is not coincident with the first bone pin hole 430 of the Chevron stage two guide body 420. Furthermore, the first and second exit paths 450 and 460 of the first and second saw slots 20 and 30, respectively, are not located directly underneath the entry points of the saw slots 20 and 30, but exit at an angle which converges above the Chevron stage two guide body 420, and diverges below the body 420. That is, a long saw blade inserted into first saw slot 20 will intersect with a similar saw blade inserted into second saw slot 30. The pair of saw slots, first saw slot 20 and second saw slot 30, are not parallel to the pair of bone pin holes, first bone pin hole 430 and second bone pin hole 440 of the Chevron stage two guide body 420.

Figure 17C:
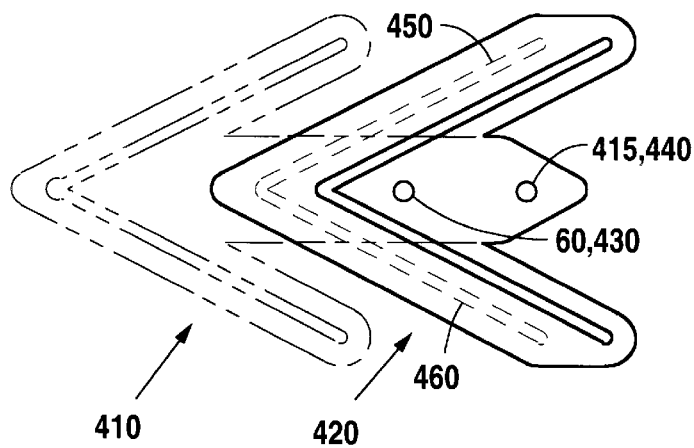

FIG. 17C depicts a top view of the Chevron stage two guide body 420 superimposed on a phantom view of the Chevron stage one guide body 410. Here it can be clearly seen that a saw blade entering the first saw slot 20 of the Chevron stage two guide body will exit at an angle back toward the dorsal Chevron stage one osteotomy cut. Similarly, a saw blade entering the second saw slot 30 of the Chevron stage two guide body will exit at an angle back toward the plantar Chevron stage one osteotomy cut. The angle of the first and second exit paths 450 and 460 can be varied to suit the preference of the surgeon and the amount of correction necessary, and will result in various sizes of pie-shaped bone wedges being removed from the dorsal and plantar Chevron cuts.

While the instant invention has been described as used in the repair of a hallux valgus deformity, it should be apparent to those skilled in the art that the invention can also be applied to the repair of many other bone structures, including those of the hands, arms and legs. The guide bodies illustrated herein make it possible for the surgeon to effect various corrective procedures in a minimal amount of time and therefore, at a reduced cost to the patient. In addition, while the use of mosquito hemostats as fixation devices has been specifically described, other devices, such as clamps, adhesives, or other known means of preventing the migration of the guide body along the K-wire shaft can be used. The various osteotomy guides described herein can be used at various angles and various positions as they are mounted to the bones of the foot, as well as to other areas of the body where they can be applied. They can also be employed in various sizes, i.e. various slot lengths and outside diameter variations to be used for both smaller and larger bones in the human body. Also, various angles can be produced within any range from 0 to 180 degrees maintaining the same basic structural configuration. Slot widths will vary depending on the size of the guide and the type of saw and saw blade used for the corresponding procedures.

The preferred embodiment of the present invention is now fully described. The above description, however, is only illustrative of the invention and is not intended to limit the invention in spirit or scope. Only the following claims and their equivalents limit the scope of the invention.

I claim:

1. An osteotomy guide comprising,
 a body having a first saw slot, a second saw slot, and a multiplicity of bone pin holes, and first and second saw slots converging at an angle of less than 180 degrees to intersect at an apex, said apex and said first and second saw slots defining a planar arcuate area, and one of said multiplicity of bone pin holes being disposed within and perpendicularly to said defined planar arcuate area.

2. The osteotomy guide of claim 1, wherein
 one of said bone pin holes is located coincident with said apex and perpendicular to said defined planar arcuate area, and one other of said bone pin holes is located along an axis originating at said apex and bisecting said arcuate area.

3. The osteotomy guide of claim 1, wherein said angle is from about 40 to about 60 degrees.

4. The osteotomy guide of claim 1, wherein said angle is approximately 55 degrees.

5. The osteotomy guide of claim 1 further comprising a third saw slot originating at a point along said second saw slot and continuing along an axis parallel to said first saw slot.

6. The osteotomy guide of claim 5, wherein
 one of said bone pin holes is located coincident with said apex and perpendicular to said defined planar arcuate area, and one other of said bone pin holes is located along an axis originating at said apex and bisecting said arcuate area.

7. The osteotomy guide of claim 6, wherein said angle is from about 40 to about 60 degrees.

8. The osteotomy guide of claim 6, wherein said angle is approximately 55 degrees.

9. The osteotomy guide of claim 5, wherein said guide includes a visualizer having a key and an indicator arm, said key being formed so as to fit interchangeably within said first, said second, or said third saw slots, and said indicator arm extending along an axis coincident with a selected one of said slots.

10. The osteotomy guide of claim 1, wherein said guide includes a visualizer having a key and an indicator arm, said key being formed so as to fit interchangeably within said first or said second saw slots, and said indicator arm extending along an axis coincident with a selected one of said slots.

11. The osteotomy guide of claim 1, wherein two of said bone pin holes are located coincident with an axis originating at a point along said first saw slot and continuing along line perpendicular to said first saw slot; said two of said bone pin holes being perpendicular to said defined planar arcuate area.

12. The osteotomy guide of claim 11, wherein said angle is from about 95 to about 115 degrees.

13. The osteotomy guide of claim 11, wherein said angle is approximately 105 degrees.

14. The osteotomy guide of claim 1, wherein said guide includes a second stage body further comprising:
   a pair of saw slots and a pair of bone pin holes, said pair of bone pin holes being coincident with a selected pair of said multiplicity of bone pin holes, and said pair of saw slots being not parallel to said pair of bone pin holes.

15. An osteotomy guide comprising,
   a body having a first saw slot, a second saw slot, and a multiplicity of bone pin holes, said first and second saw slots converging at an angle of not greater than 180 degrees to intersect at an apex, said apex and said first and second saw slots forming an arcuate area, and at least one of said multiplicity of bone pin holes being disposed within said arcuate area, wherein said guide includes a visualizer having a key and an indicator arm, said key being formed so as to fit interchangeably within said first or said second saw slots, and said indicator arm extending along an axis coincident with a selected one of said slots.

16. An osteotomy guide comprising,
   a body having a first saw slot, a second saw slot, and a multiplicity of bone pin holes, said first and second saw slots converging at an angle of not greater than 180 degrees to intersect at an apex, said apex and said first and second saw slots forming an arcuate area, and at least one of said multiplicity of bone pin holes being disposed within said arcuate area; and
   a third saw slot originating at a point along said second saw slot and continuing along an axis parallel to said firs saw slot wherein said guide includes a visualizer having a key and an indicator arm, said key being formed so as to fit interchangeably with said first, and second, or said third saw slots, said indicator arm extending along an axis coincident with a selected one of said slots.

17. An osteotomy guide comprising,
   a body having a first saw slot, a second saw slot, and a multiplicity of bone pin holes, said first and second saw slots converging at an angle of not greater than 180 degrees to intersect at an apex, said apex and said first and second saw slots forming an arcuate area, and at least one of said multiplicity of bone pin holes being disposed within said arcuate area, wherein said angle is 180 degrees and said first and second saw slots are not parallel to said multiplicity of bone pin holes, and wherein said guide includes a visualizer having a key and an indicator arm, said key being formed so as to fit interchangeably within said first, and second slots, said indicator arm extending along an axis coincident with a selected one of said slots.

18. An osteotomy guide comprising,
   a body having a first saw slot, a second saw slot, and a multiplicity of bone pin holes, said first and second saw slots converging at an angle of not greater than 180 degrees to intersect at an apex, said apex and said first and second saw slots forming an arcuate area, and at least one of said multiplicity of bone pin holes being disposed within said arcuate area; and
   a second stage body further comprising a pair of saw slots and a pair of bone pin holes, said pair of bone pin holes being coincident with a selected pair of said multiplicity of bone pin holes, said pair of saw slots being not parallel to said pair of bone pin holes.

19. An osteotomy guide comprising,
   a body having a first saw slot, a second saw slot, and a multiplicity of bone pin holes, said first and second saw slots converging at an angle of less than 180 degrees to intersect at an apex, said apex and said first and second saw slots forming an arcuate area, and at least one of said multiplicity of bone pin holes being disposed within said arcuate area, wherein at least two of said bone pin holes are located coincident with an axis originating at a point along said first saw slot and continuing along a line perpendicular to said first saw slot; and
   a second stage body further comprising a single saw slot and a pair of bone pin holes, said pair of bone pin holes being coincident with a selected pair of said multiplicity of bone pin holes, said single saw slot coincident with said first saw slot and said single saw slot being not parallel to said to said center lines of said pair of bone pin holes.

* * * * *